(12) United States Patent
Fetzer

(10) Patent No.: US 7,254,519 B2
(45) Date of Patent: Aug. 7, 2007

(54) MULTI CHANNEL MULTIPLEXED INSPECTION SYSTEM AND METHOD

(75) Inventor: Barry A. Fetzer, Renton, WA (US)

(73) Assignee: The Boeing Company, Chicago, IL (US)

( * ) Notice: Subject to any disclaimer, the term of this patent is extended or adjusted under 35 U.S.C. 154(b) by 177 days.

(21) Appl. No.: 10/949,625

(22) Filed: Sep. 24, 2004

(65) Prior Publication Data

US 2006/0074577 A1   Apr. 6, 2006

(51) Int. Cl.
*G21C 17/013* (2006.01)

(52) U.S. Cl. .................................. 702/183; 73/602

(58) Field of Classification Search .................. 702/57, 702/62, 64, 69, 75, 77–81, 83, 93, 104, 116, 702/122, 159, 171, 183, 189, 191, 16; 73/602, 73/631; 356/432; 340/561; 375/360
See application file for complete search history.

(56) References Cited

U.S. PATENT DOCUMENTS

| | | | |
|---|---|---|---|
| 3,789,350 A * | 1/1974 | Rolle | 367/11 |
| 3,958,451 A | 5/1976 | Richardson | |
| 4,103,234 A * | 7/1978 | Frazier, Jr. | 375/360 |
| 4,160,386 A | 7/1979 | Jackson et al. | |
| 4,167,880 A | 9/1979 | George | |
| 4,173,897 A | 11/1979 | Förstermann et al. | |
| 4,173,898 A | 11/1979 | Förstermann et al. | |
| 4,229,796 A | 10/1980 | Garrett | |
| 4,311,052 A | 1/1982 | Jeffras et al. | |
| 4,327,588 A | 5/1982 | North | |
| 4,365,514 A | 12/1982 | Ho | |
| 4,470,304 A | 9/1984 | Nusbickel, Jr et al. | |
| 4,752,895 A | 6/1988 | Sarr | |
| 4,755,953 A | 7/1988 | Geithman et al. | |
| 4,803,638 A * | 2/1989 | Nottingham et al. | 702/36 |
| 4,912,411 A * | 3/1990 | Allison et al. | 324/235 |
| 5,047,771 A * | 9/1991 | Engeler et al. | 341/140 |
| 5,241,135 A | 8/1993 | Fetzer | |
| 5,396,890 A * | 3/1995 | Weng | 600/443 |
| 5,417,218 A * | 5/1995 | Spivey et al. | 600/448 |

(Continued)

OTHER PUBLICATIONS

*Maxim CMOS RF/Video Multiplexers*, MAX310/311, Maxim Integrated Products, (undated), available at http://pdfserv.maxim-ic.com/en/ds/MAX310-MAX311.pdf (Sep. 24, 2004), 7 pages.

(Continued)

*Primary Examiner*—Carol S. W. Tsai
*Assistant Examiner*—Mohamed Charioui
(74) *Attorney, Agent, or Firm*—Alston & Bird LLP

(57) ABSTRACT

Provided are systems and methods for multi-channel non-destructive inspection which provide high data throughput, logarithmic amplification of large dynamic range, and simplicity of supporting electronics. More specifically, provided are systems and methods for inspecting a structure that may use an interface board, two pulser boards, each coupled to 16 transmit channels, and two receiver boards, each coupled to 16 receive channels, where the receiver boards are capable of processing data from the 32 receive channels by logarithmically amplifying at least 70 dB of dynamic range. A receiver board may include a serial connection of two layers of multiplexing switches to provide 70 dB isolation between channels, a logarithmic amplifier for logarithmically amplifying 70 dB of dynamic range, a linear amplifier, and an analog-to-digital converter.

49 Claims, 2 Drawing Sheets

U.S. PATENT DOCUMENTS

| | | | |
|---|---|---|---|
| 5,485,084 | A | 1/1996 | Duncan et al. |
| 5,593,633 | A | 1/1997 | Dull et al. |
| 5,621,414 | A * | 4/1997 | Nakagawa ............... 342/350 |
| 5,963,882 | A | 10/1999 | Viertl et al. |
| 5,986,549 | A * | 11/1999 | Teodorescu ............ 340/561 |
| 6,057,927 | A * | 5/2000 | Levesque et al. ........ 356/432 |
| 6,220,099 | B1 | 4/2001 | Marti et al. |
| 6,474,164 | B1 * | 11/2002 | Mucciardi et al. ......... 73/602 |
| 6,484,583 | B1 | 11/2002 | Chennell et al. |
| 6,722,202 | B1 | 4/2004 | Kennedy et al. |
| 6,725,721 | B2 | 4/2004 | Venczel |
| 6,839,636 | B1 * | 1/2005 | Sunshine et al. .......... 702/22 |

OTHER PUBLICATIONS

*24-Bit Dual-Axis Quadrature Counter*, LS7266R1, LSI Computer Systems, Inc., May 2004, available at http://me.in-berlin.de/~urmel/robot/docu/LS7266R1.pdf (Sep. 24, 2004), 14 pages.

*Fast Technologies for Ultrasonic Non Destructive Evaluation-Analog Modules*, Oct. 1997, http://www.iai.csic.es/users/end/am.html available Jul. 16, 2004, 3 pages.

*MS-8 Multiplexer for Multichannel Ultrasonic Testing*, Technical Information, AGFA Krautkramer Ultrasonic Systems, Jun. 2002, 2 pages.

*USIP 20 GP The Ultrasonic Systems Instrument for Automated Testing*, Krautkrämer, Jun. 1994, 12 pages.

*MUX D Multiplexer for Multichannel Ultrasonic Testing*, Krautkramer, Jul. 1998, 2 pages.

*TTU02-MUX Standalone/Rack*, Fractional T1, 2 or 4 Port Multiplexer, available at http://www.megatelindustries.com/ttu02_mux.pdf (Sep. 24, 2004), 2 pages.

*Real-time Portable G-Scan System*, NDT Solutions Ltd. 2 pages.

*MUX 8 Ultrasonic Systems Multiplexer*, Ultrasonic Sciences Ltd., Jun. 1998, 2 pages.

*High Speed Large Area Scanning Using Air-Coupled Ultrasound*, J. O. Strycek et al., http://www.qmi-inc.com/High%20Speed%20Large%20Area%20Scanning%20using%20... available Jul. 12, 2004, 5 pages.

*Multi-Channel Multiplexer*, GE Inspection Technologies, http://www.geinspectiontechnologies.com/products//Ultrasonics/Multiplexers/index.html available Aug. 30, 2004, 3 pages.

*Ultrasonics*, GE Inspection Technologies, http://www.geinspectiontechnologies.com/products/Ultrasonics/index.html available Aug. 03, 2004, 1 page.

*Ultrasonic Systems and Testing Machines*, GE Inspection Technologies, http://www.geinspectiontechnologies.com/solutions/TestingMachines/Ultrasonics/index.h... available Aug. 3, 2004, 3 pages.

*RapidScan Rapid C-Scanning*, NDT Solutions, Ltd., http://www.ndtsolutions.com/rscan.htm available Aug. 5, 2004, 2 pages.

*Rapid Scan Specification*, NDT Solutions Ltd., http://www.ndtsolutions.com/spec_rscan.htm, Aug. 05, 2004, 3 pages.

*Mechanical Engineering*, http://www.fen.bris.ac.uk/faculty/publicity/april04brief/page20.html available Aug. 05, 2004, 2 pages.

*Integrated Ultrasonic Arrays for Rapid Manual Inspection and Mapping*, D. Lines, http://www.diagnosticsonar.com/english/industrial/publications/rapidarray.html available Aug. 05, 2004, 17 pages.

*SWIM*, http://www.wavesinsolids.com/intelligent_ultrasonics.htm, available Sep. 24, 2004, 4 pages.

* cited by examiner

MULTI CHANNEL MULTIPLEXED INSPECTION SYSTEM AND METHOD

FIELD OF THE INVENTION

The present invention relates generally to an apparatus and method for inspecting a structure and, more particularly, to an apparatus and method for inspecting a structure that provides multiple multiplexed channels for non-destructive inspection of a structure.

BACKGROUND

Non-destructive inspection (NDI) of structures, also referred to as non-destructive testing (NDT), involves thoroughly examining a structure without harming the structure or requiring significant disassembly of the structure. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly utilized in the aircraft industry to inspect aircraft structures for any type of internal or external damage to or flaws in the structure. Inspection may be performed during manufacturing of a structure and/or once a structure is in-service. For example, inspection may be required to validate the integrity and fitness of a structure for continued use in manufacturing and future ongoing use in-service. However, access to interior surfaces is often more difficult or impossible without disassembly, such as removing a part for inspection from an aircraft.

Among the structures that are routinely non-destructively tested are composite structures, such as composite sandwich structures and other adhesive bonded panels and assemblies, including, but not limited to, fuselage frames and shear ties, wing stringers, floor beams, flange and radius sections of horizontal stabilizer ribs, and floor stanchions. In this regard, composite structures are commonly used throughout the aircraft industry because of the engineering qualities, design flexibility and low weight of composite structures, such as the stiffness-to-weigh ratio of a composite sandwich structure. As such, it is frequently desirable to inspect composite structures to identify any foreign material or flaws, such as cracks, voids or porosity, which could adversely affect the performance of the composite structure. For example, typical flaws in composite sandwich structures, generally made of one or more layers of lightweight honeycomb or foam core material with composite or metal skins bonded to each side of the core, include disbonds which occur at the interfaces between the core and the skin or between the core and a septum intermediate skin.

Various types of sensors may be utilized to perform non-destructive inspection. One or more sensors may move over the portion of the structure to be examined, and receive data regarding the structure. For example, a pulse-echo (PE), through- or thru-transmission (TT), or shear wave sensor may be utilized to obtain ultrasonic data, such as thickness gauging, detection of laminar defects and porosity, and/or crack detection in the structure. Resonance, pulse echo or mechanical impedance sensors may be utilized to provide indications of voids or porosity, such as in adhesive bond lines of the structure. High resolution inspection of aircraft structure are commonly performed using semi-automated ultrasonic testing (UT) to provide a plan view image of the part or structure under inspection. While solid laminates may be inspected using one-sided pulse echo ultrasonic testing (PEU), composite sandwich structures typically require through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure to be inspected such as opposite surfaces of a composite material. An ultrasonic signal is transmitted by at least one of the transducers, propagated through the structure, and received by the other transducer. Data acquired by sensors, such as TTU transducers, is typically processed by a processing element, and the processed data may be presented to a user via a display.

In order to increase the rate or speed at which the inspection of a structure is conducted, the scanning system may include ultrasonic probes that have arrays of ultrasonic transmitters and receivers or arrays of probes with one or more ultrasonic transmitters and receivers. Typically each "channel" in an array refers to a transducer-receiver pairing and includes a transmit channel to the transducer and a receive channel from the receiver. Generally, the more channels available, the more physical coverage of a part which can be scanned. As such, the inspection of the structure can proceed more rapidly and efficiently, thereby reducing the costs associated with the inspection.

TTU sensors, i.e., TTU transducers and receivers, may be controlled by a variety of systems, including systems which permit multiple TTU transducers and receivers to be used in a single probe, an array of probes, or a combination thereof. The more TTU transducer and receiver pairings, the faster a part may be scanned, presuming the control system can keep up with the data transmissions provided by the TTU transducers and receivers. TTU systems which include numerous TTU transducers and receivers are referred to as having a corresponding number of channels, one channel referring to a transducer-receiver pairing. Multi-channel TTU systems are typically expensive to fabricate, in part because they include a separate RF amplifier and envelope (peak) detector for each receive channel of ultrasound data from a TTU transceiver-receiver pairing. Further, typical multi-channel TTU systems use an individual pulser circuit for each channel, requiring a tremendous amount of space to house and wire numerous channels together. Often multi-channel systems are housed in large racks of electronic components. In addition to expensive costs and large size requirements, maintaining multi-channel systems has typically been problematic and expensive. Typical multi-channel TTU systems may be difficult to troubleshoot because of the number of individual components and extensive wiring required in addition to often obsolete components. Further, typical multi-channel TTU systems are limited to communicating processed signals as 8 bit resolution digital data due to slow processing and/or communication paths and are electronically noisy due to the high number of RF cables which are used to couple the individual components together.

Accordingly, a need exists for an improved system and method for multi-channel non-destructive inspection which provides high data throughput, large dynamic range, and simplicity of supporting electronics.

SUMMARY OF THE INVENTION

In light of the foregoing background, embodiments of the present invention provide improved systems and methods for multi-channel non-destructive inspection which provide high data throughput, large dynamic range, and simplicity of supporting electronics.

According to one advantageous embodiment of the present invention, a system is provided which includes an interface board, at least one pulser board, a plurality of transmit channels, at least one receiver board, and a plurality of receive channels. The interface board connects to the pulser board, which connects to the transmit channels. The interface board also connects to the receiver board, which connects to the receive channels. The receiver board may include a logarithmic amplifier for logarithmically amplifying signals from a plurality of receive channels for at least 70 decibels (dB) of dynamic range. The receiver board may also include a tuned filter connected to each of the receive channels to filter the signal received over the receive channel to a desired frequency, such as 5 MHz. The receiver board and interface board may be capable of processing the signals from the receive channels at a resolution of 12-bits. The interface board and pulser board may be capable of communicating data to transmit channels at a channel cycling rate of 200 microseconds (µs) per transmit channel, such as a cycling rate of 5 kHz to cycle through all of the transmit channels once every 6.4 milliseconds (ms) where 32 transmit channels are used. The receiver board may also be capable of receiving and processing data from receive channels at a channel cycling rate of 200 microseconds (µs) per receive channel.

The interface board may be connected to a remote device such as a computer with a microprocessor by way of an Ethernet connection capable of transmitting 12-bit resolution scan data in real time. The interface board may be further capable of interfacing with data encoders such as by the use of an encoder interface coupled to the interface board and capable of receiving data from encoders to provide the data to the interface board. The encoder interface may include one or more counter chips. The encoder interface may be capable of receiving data such as position data, speed data, velocity data, and distance data.

According to another advantageous embodiment of the present invention, a system for inspecting a structure includes an interface board, two pulser boards, each coupled to 16 transmit channels, and two receiver boards, each coupled to 16 receive channels, where the receiver boards are capable of processing data from the 32 receive channels by logarithmically amplifying signals from the receive channels for at least 70 decibels (dB) of dynamic range. A pulser board may be a printed circuit board (PCB) and may include 16 pulsers, one for each of 16 transmit channels.

A receiver board of an advantageous embodiment of the present invention comprises, in addition to a logarithmic amplifier, a multiplexer for providing 70 dB of isolation between receive channels and may be capable of processing data from a plurality of receive channels with 70 dB of isolation provided by the multiplexer and with logarithmic amplification of 70 dB of dynamic range by the logarithmic amplifier. A multiplexer may be a series of multiplexing chips, also referred to as multiple layers of multiplexing switches. 70 dB of isolation between channels may be provided, for example, by a 60 dB multiplexing chip serially coupled to a 10 dB multiplexing chip. A multiplexing chip may be capable of switching between receive channels. The logarithmic amplifier may be capable of providing logarithmic amplification from −67 dB to +3 dB.

In a further advantageous embodiment of the present invention, a receiver board may include the logarithmic amplifier serially coupled to a linear amplifier. The linear amplifier may be capable of providing 20 dB of linear amplification.

A further advantageous embodiment of a system for inspecting the structure of the present invention may include an interface board, at least one pulser board, a plurality of transmit channels, at least one receiver board, and a plurality of receive channels. The interface board connects to the pulser board, which connects to the transmit channels. The interface board also connects to the receiver board, which connects to the receive channels. The receiver board may be capable of processing data from the plurality of receive channels with at least 70 dB of logarithmic gain. The receiver board may also include a plurality of tuned filters, one of the tuned filters coupled to each of the receive channels, a multiplexer serially coupled to the plurality of tuned filters, a logarithmic amplifier serially coupled to the multiplexer, a linear amplifier serially coupled to the logarithmic amplifier, and an analog-to-digital converter serially coupled to the linear amplifier. The receiver board may also include an envelope peak detector serially coupled between the linear amplifier and the analog-to-digital converter, for capturing the voltage peaks of the signal that has been multiplexed, logarithmically amplified, and linearly amplified. The receiver board may also include a diode, serially coupled between the linear amplifier and the envelope peak detector, for isolating positive voltage from the signal that has been multiplexed, logarithmically amplified, and linearly amplified. The multiplexer may include a series of multiplexing chips, where 70 dB of isolation between channels may be provided by a first layer formed of a 60 dB multiplexing chip serially coupled to a second layer formed of one or more 10 dB multiplexing chips and where the multiplexer may be capable of switching between the receive channels. Where a single 60 dB multiplexing chip may be used to switch between 16 receive channels, two 10 dB multiplexing chips may be used to switch between 8 receive channels.

A 32 channel multiplexing system for inspecting a structure of an advantageous embodiment of the present invention may include 32 transmit transducers, 32 receive transducers, 32 receive channels, and a multiplexing system. The 32 receive transducers are communicably coupled to receive ultrasonic signals through a structure under inspection that are transmitted by the 32 transmit transducers. The 32 receive transducers are individually coupled to the 32 receive channels which are coupled to the multiplexing system to process the ultrasonic signals received by the 32 receive transducers and transmitted through the 32 receive channels. The multiplexing system comprises a logarithmic amplifier and may be capable of processing data by logarithmically amplifying each channel with at least 70 dB of dynamic range. Each transmit transducer may include a pulsing sensor, and each receive transducer may include a receiving sensor communicably coupled to a corresponding pulsing sensor. Each pulsing sensor may be coupled to a transmit channel, and each receiving sensor may be coupled to a receive channel. The 32 channel multiplexing system may also include an interface for remote communication to an analysis computer. The multiplexing system may be adapted to switch between receive channels. The multiplexing system may be further adapted to filter the data received from the receive channels before switching and logarithmically amplifying the data. The multiplexing system may be further capable of linearly amplifying the data that has been previously processed with logarithmic amplification of at least 70 dB of dynamic range. The linear amplification may have a 20 dB gain. The multiplexing system may be further capable of converting from analog to digital the data that has been previously processed with logarithmic amplification and linear amplification.

A method for multiplexing channels of an inspection system of an advantageous embodiment of the present invention is provided which includes the steps of receiving signals from a plurality of receive channels following propagation through a part under inspection, and multiplexing the received signals. The step of multiplexing received signals includes the steps of filtering the received signals, switching between the receive channels to select one receive channel and define a switched received signal, logarithmically amplifying the switched received signal, linearly amplifying the switched, logarithmically amplified received signal, and converting the switched, logarithmically amplified, linearly amplified received signal from analog to digital. The step of logarithmically amplifying the switched received signal may include the step of providing logarithmic amplification for at least 70 dB of dynamic range, such as providing amplification from −67 dB to +3 dB. An embodiment of a method may also include the step of transmitting signals to a plurality of transmit channels. The method may also include the steps of controlling timing requirements for the step of transmitting signals to a plurality of transmit channels, and transmitting the multiplexed signals in real time to a remote processor. The step of transmitting the multiplexed signals in real time to a remote processor may include the step of transmitting the multiplexed signals from the receive channels at a cycling rate of 200 microseconds (μs) per receive channel, such as a cycling rate of 5 kHz to cycle through all of the receive channels once every 6.4 milliseconds (ms) where 32 transmit channels are used, where the multiplexed signal is processed and transmitted with a resolution of 12 bits. The step of transmitting signals to a plurality of transmit channels may include the step of communicating data to the transmit channels at a cycling rate of 200 microseconds (μs) per transmit channel, such as, at a cycling at a rate of 5 kHz through all of the transmit channels once every 6.4 milliseconds (ms) where 32 channels are used. The method may also include the step of processing multiplexed signals from the receive channels at 12 bits through all of the receive channels once every 6.4 milliseconds (ms), at a cycling at a rate of 5 kHz where 32 channels are used. A method may also include the step of capturing peak voltage. The method may further include the step of isolating positive voltage for capturing peak voltage.

These and other characteristics, as well as additional details, of the present invention are further described herein with reference to these and other embodiments.

BRIEF DESCRIPTION OF THE DRAWING

Figure 1:
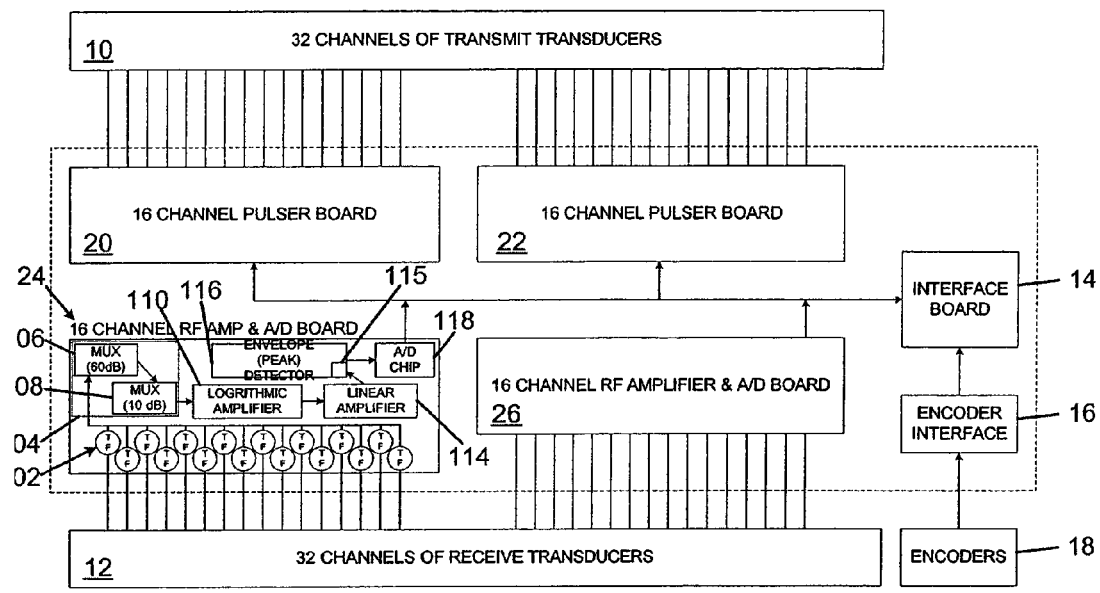
Figure 2:
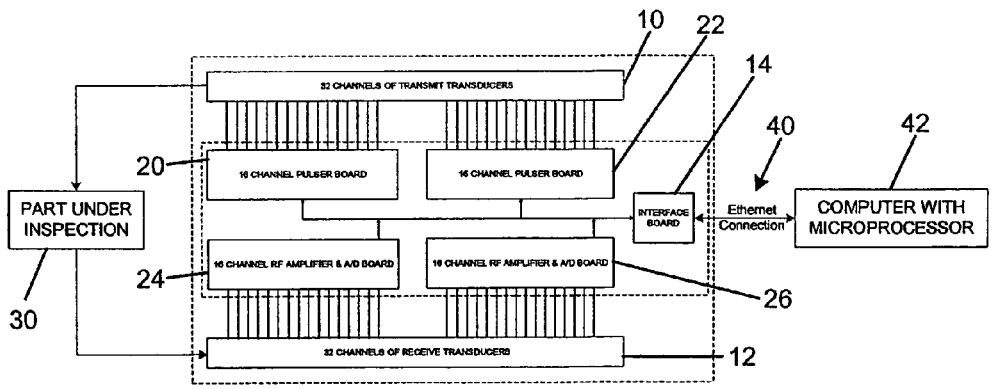
Figure 3:
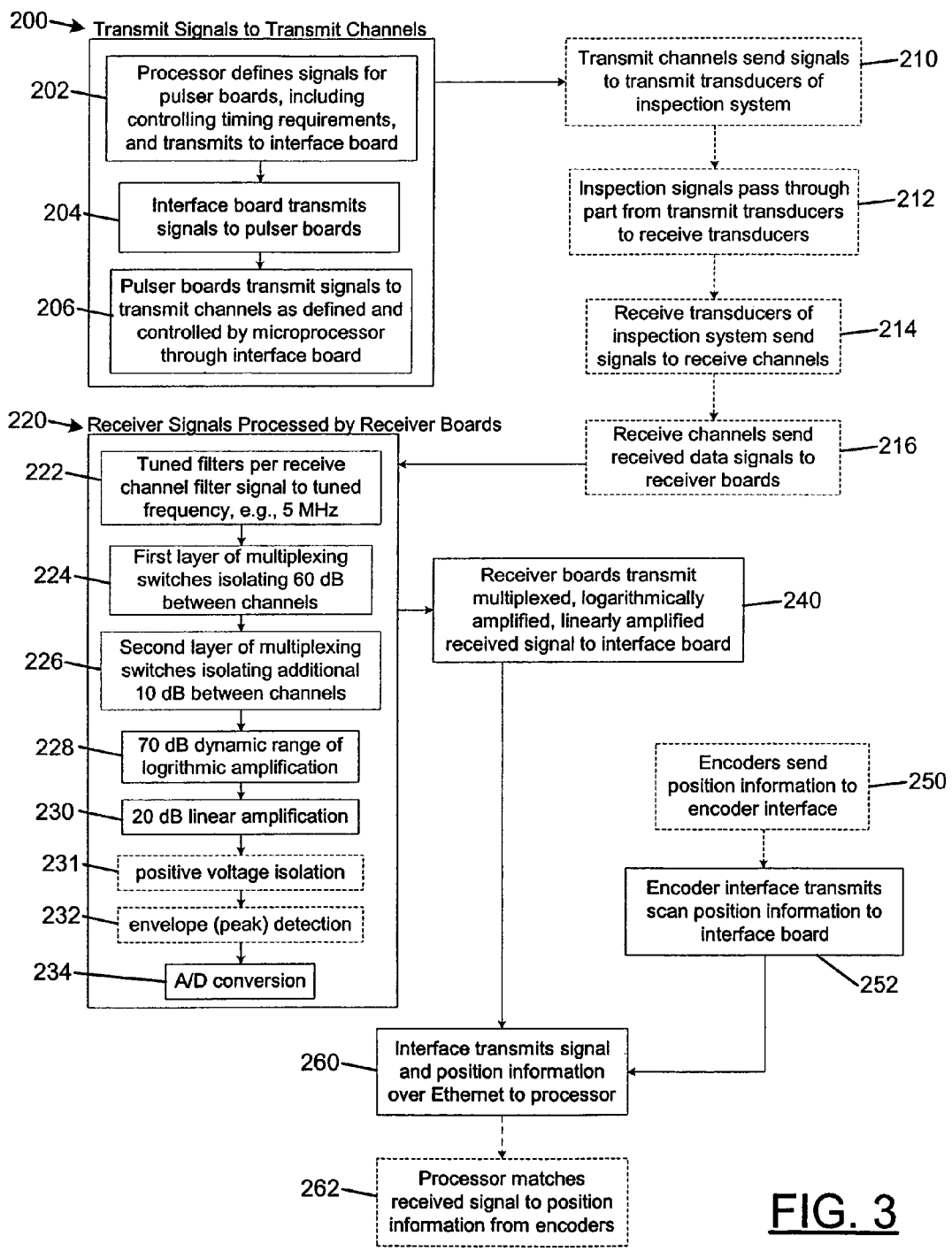

Having thus described the invention in general terms, reference will now be made to the accompanying drawing, which is not necessarily drawn to scale, and wherein:

FIG. 1 is a schematic block diagram of a 32 channel multiplexed TTU system of an embodiment of the present invention;

FIG. 2 is a schematic block diagram of a 32 channel multiplexed TTU system connected to a remote processor using an Ethernet connection of an embodiment of the present invention; and FIG. 3 is a flow diagram of an embodiment of a 32 channel multiplexed TTU system of an embodiment of the present invention.

DETAILED DESCRIPTION

The present inventions will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers and variables refer to like elements and parameters throughout.

Embodiments of the present invention may be particularly useful in the aircraft industry for composite structure inspection; further embodiments of the present invention may also be useful in many domains and for a variety of other applications, including, for example, manufacturing of rockets and inspection of composite sandwich structure.

Although specifically designed for through-transmission ultrasonic (TTU) inspection or testing, embodiments of the present invention could be used for other inspection techniques, such as pulse echo non-destructive inspection. Further, although specifically designed for 32 channel TTU systems, embodiments of the present invention may be advantageously used to produce a TTU system with fewer than 32 channels, such as a 16-channel embodiment, or embodiments of the present invention may be combined to be advantageously used to produce a TTU system with more than 32 channels, such as 64-channel and 128-channel embodiments where two and four 32 channel systems, respectively, are connected to an Ethernet hub. If a multichannel system has more than 32 channels, a conventional Ethernet communication connection may require that data is buffered on the transmitting end to account for the bandwidth of the Ethernet link.

The terms "non-destructive inspection" (NDI) and "non-destructive testing" (NDT) are used synonymously herein.

FIG. 1 is a schematic block diagram of a 32 channel multiplexed TTU system of an embodiment of the present invention. The system includes 32 pairs of corresponding transducers. Of the 64 transducers, 32 transducers are transmitting transducers 10 or pulsing transducers on one side of a component or structure under inspection. The other 32 transducers are receiving transducers 12 on the opposing side of the structure under inspection. Thus, 32 channels are provided for 32 transmit transducers 10 and 32 channels are provided for 32 receive transducers 12. As used herein, a "channel" refers to the communication link to a transducer. The transducers may be included in one device or probe. Alternatively, the plurality of channels may be divided in such a manner as to function as an array of probes, such as a 64 probe array with 32 transmitting probes and 32 receiving probes, where each probe includes one transducer. Each transmit or receive channel corresponds with an individual piezoelectric crystal transducer; although, the present invention could be used where one or more transducers correspond to one or more transducers. The individual transducers, as described, may be arranged as in a single probe or a number of probes functioning in an array. Each of the 32 transmit channels 10 may be sequentially pulsed, such as a pulser board pulsing channels 1 through 32, one channel every 200 microseconds (μs), at a 5 kHz repetition rate to cycle through the 32 channels 10 once every 6.4 milliseconds (ms). A pulser board pulsing channels refers to the pulser board providing a transmit signal to a transmit channel for a transducer. An example pulser board, or interface board or receiver board, may be a printed circuit board (PCB) with electrical connections or communication paths. The interface board 14, and/or a processor or microcontroller of an attached computer (not shown), may be used to control the sequential pulsing of the 32 transmit channels 10 and coordination of the sequence of received signals. The repetition rate for the cycling of channels is typically selected, and limited, in part due to the time for an ultrasonic signal to propagate from a transmitting transducer crystal through a couplant to the surface of the part, through the part under inspection, and from the surface of the part through a couplant to a receiving transducer crystal. The repetition rate may also be dependent upon such factors as the communication bandwidth to transmit the processed signals from the multiplexing receiver board to a computer controlling and/or processing the inspection.

The embodiment of the present invention shown in FIG. 1 shows two 16 channel pulser boards 20, 22, each connected to an interface board 14 and each providing 16 of the 32 transmit channels 10. A pulser board typically is a PCB board which can independently provide signals intended for the 16 different transducers from an interface board to the 16 corresponding channels using corresponding pulsers of the pulser board which provide electronic pulse signals for the digital or electronic signals from the interface board. Also included are two 16 channel receiver boards or RF amplifier and A/D boards 24, 26, each coupled to the interface board 14 and each receiving 16 of the 32 receive channels 12. A receiver board of the present invention and the electronics thereof are described more fully below. A 32 channel multiplexed TTU system as shown in FIG. 1 may also include an encoder interface 16 to provide an interface between positional encoders 18 of a scanning system and an interface board 14 of the 32 channel multiplexed TTU system. An encoder interface 16 may include two counter chips, such as LS7266R1 counter chips manufactured by LSI Computer Systems, Inc., of Melville, N.Y. The counter chips have internal registers which hold the current value as an encoder on the scanning system moves back and forth with a scanning probe. The counter chips will count up and down from a reference value to provide different values for the internal registers of the counter chips. This information is typically referred to as position information of the scanning system. The position information is relative to the position of the transducers in some physical manner because the encoders are mechanically tracking the movement of the transducers. Thus, the position information provided by an encoder is synchronous to the movement of a scanning probe, but the transducer signals are asynchronous to the scanner movement. Thus by combining the position information of the encoder through an encoder interface, a microprocessor is capable of tying the two pieces of information together to establish the position of a transducer for a particular ultrasonic signal. For example, a microprocessor may combine positional information from the counter chips of the encoder interface into the same data packet as the corresponding ultrasonic data. Additional software may then be able to analyze the particular data packet as having an ultrasonic data value at a specific position which occurred during the scan. Although encoders are typically used to provide position information, encoders may additionally or alternatively be used to provide such data as speed data, velocity data, and distance data.

A receiver board 24, 26 may include a tuned filter 102 for each receive channel 12. For example, a tuned filter 102 may include a base amplifier and a tank circuit. A tunable capacitor of a tuned filter 102 may be adjusted to filter the received signal to a specific frequency, such the frequency of a piezoelectric crystal oscillating at 5 MHz. After filtering each of the received signals, all 16 signals are provided to a first layer of multiplexing switches 106, referred to as a first multiplexing chip. As a non-limiting example, a multiplexing chip may be a MAX310CPE multiplexing chip manufactured by Maxim Integrated Products, Inc., of Sunnyvale, Calif., which permits a signal voltage input range of 15 volts peak-to-peak (Vpp). The first layer of multiplexing switches 106 may provide 60 dB of isolation between the 16 signals. A second layer of multiplexing switches 108, also referred to as a second multiplexing switch may provide an additional 10 dB of isolation between the channels. The second layer of multiplexing switches 108 may also use MAX310CPE multiplexing switches. Using two layers of multiplexing switches 108 can achieve 70 dB of isolation between the channels. With 70 dB of isolation between channels, one channel can be 3000 times greater than another channel without affecting the smaller input as provided by 70 dB=20×Log(difference) where (difference) is equal to 3000 for 70 dB. For example, one channel can have a 5 MHz signal with a strength of 1 millivolt (mV) and another channel can have a 5 MHz signal with a 3 volt (V) strength without affecting the 1 mV signal. Also, by separating the multiplexing switches into two layers, the capacitance is decreased so as not to degrade the RF signal. Different combinations of channel switching may be used with the two layers of multiplexing switches. For example, a single 60 dB multiplexing chip used to switch between 16 channels may be used with two 10 dB multiplexing chips to switch between 8 channels each. By selecting corresponding channels in the first layer of multiplexing switches 106 and the second layer of multiplexing switches 108, a single receive channel may be selected.

The single receive channel signal, filtered and multiplexed, is provided to a logarithmic amplifier 110 which provides logarithmic amplification for 70 dB of dynamic range, such as a voltage range of −67 dB to +3 dB, although logarithmic amplification can be centered around different dynamic ranges. Thus, the layered multiplexing chips 106, 108 provide the full dynamic range of the capabilities of the logarithmic amplifier 110. Logarithmic amplification follows the formula $Gain_{log}=20\times Log(V_{out}/V_{in})$. After logarithmic amplification, the signal may be linearly amplified by a linear amplifier 114, such as to provide 20 dB of linear amplification to adjust the logarithmically amplified signal to the full range of an analog to digital converter. Linear amplification follows the formula $Gain_{lin}=(V_{out}/V_{in})$. The signal may then be converted from analog to digital using an analog to digital chip 118 (A/D converter), such as an analog to digital chip with an input of 0 to 10 volts. An envelope (peak) detector 116 and a diode 115 may be used between the linear amplification and the conversion from analog to digital such that the peak value is converted to a digital signal by the A/D converter. The diode 115 can isolate the positive voltage of the amplified signal to permit the envelope (peak) detector 116 to capture the peak amplitude of the signal. Only the peak amplitudes of a signal are required for TTU inspection to identify flaws from changing amplitudes. For example, the logarithmic amplifier 110 may output a signal with 1.4 volts peak-to-peak (Vpp) centered around 0 volts; the linear amplifier 114 may increase the signal to a 20 Vpp signal (−10 V to +10 V); the diode 115 may isolate the +10 V peak range (0 V to +10 V); the envelope peak detector 116 may capture the peak amplitudes of the signal ranging from 0 V to +10 V; and the analog to digital chip 118 may convert the 0 to 10 V signal to a digital signal with a 12 bit resolution.

The use of the large 70 dB dynamic range logarithmic amplification assists in the identification of small changes or imperfections in a part under inspection. For example, 70 dB of dynamic range may be required to find a piece of foreign material located 68 plys down in a half inch thick piece of graphite under inspection, where 1 ply, or 1 layer, is seven thousandths of an inch thick. The foreign piece of material may be almost on the bottom edge of the piece of graphite under inspection as viewed through the part from the transmitting transducer to the receiving transducer. Sound, or specifically an ultrasonic signal, diminishes as it propagates through a part under inspection. For example, in the inspection of the half inch thick piece of graphite, the ultrasonic signal may have dropped by as much as 60 dB in through transmission before it reaches the 68th ply where the piece of foreign material is located and for which 2 dB of change may be necessary to detect the presence of the piece of foreign material. In order to detect the 2 dB of change, the noise must not be so great as to mask the 2 dB change for the piece of foreign material. The dynamic range must be large enough to detect the flaw in the structure under inspection, the piece of foreign material in the graphite. By using a large logarithmic gain, a scanning system may be capable of resolving a high level of detail in a part under inspection. Using logarithmic amplification amplifies the small changes more than large changes in the signal. Typically, large changes in a signal include noise. By comparison, when using linear amplification, the noise is amplified just as much as the signal. And by using a large dynamic range, a system is capable of scanning thick parts. In addition to accounting for a high dynamic range, the system must be able to multiplex the high dynamic range without acquiring crosstalk, or noise between the channels. In order to switch or multiplex the large dynamic range signals without introducing noise or crosstalk between the channels, the multiplexing may be performed by layering multiplexing chips, such as described by using an initial 60 dB range and a second layer of 10 dB range multiplexing chips.

FIG. 2 is a schematic block diagram of a 32 channel multiplexed TTU system connected to a remote processor using an Ethernet connection of an embodiment of the present invention. As may be seen in the schematic diagram of FIG. 2, 32 transmit channels 10 may be coupled to 32 transducers which are used to inspect a part 30. 32 receive channels 12 may be coupled to 32 receive transducers to receive signals transmitted through a part under inspection 30 from 32 corresponding transmitting transducers. The multiplexed TTU system may be connected to a remote processor 42, such as a computer with a microprocessor for further processing, analyzing, and displaying results of the inspection, through a communication connection or a link, such as an Ethernet communication connection 40 or a serial communication connection, as described more fully herein.

FIG. 3 is a flow diagram of an embodiment of a 32 channel multiplexed TTU system of an embodiment of the present invention. Functions and/or elements of the flow diagram of FIG. 3 shown in broken lines may be performed by components of a TTU system which may be, but need not be, included in an embodiment of the present invention. A pulser board may be used to transmit 200 signals to transmit channels. This process may include a processor defining and sending 202 control signals for pulser boards to send pulse signals along a selected channel to the corresponding transducer, an interface board transmitting 204 the control signals to the pulser boards, and the pulser boards transmitting 206 the pulse signals to transmit channels as defined and controlled by the processor through an interface board. Once the pulse signals are transmitted 200 to the transmit channels, the transmit channels direct 210 the pulse signals to transmit transducers of the inspection system. The inspection signals then pass 212 through the part from transmit transducers to receive transducers. The inspection signals received by the receive transducers of the inspection system propagate 214 along the receive channels. The receive channels then direct 216 the received inspection signals to the receiver boards. The receiver boards then process 220 the received inspection signals. The processing of the received signals may include tuned filters on each receive channel filtering 222 the signal to a tuned frequency, such as 5 MHz, a first layer of multiplexing switches providing 60 dB of isolation 224 between channels, a second layer of multiplexing switches providing an additional 10 dB of isolation 226 between channels, logarithmic amplification 228 of 70 dB of dynamic range, linear amplification 230 of 20 dB, positive voltage isolation 231, envelope peak detection 232, and analog to digital conversion 234. The received signals which have been multiplexed, logarithmically amplified, linearly amplified, and converted from analog to digital may be transmitted 240 from receiver boards to an interface board. An embodiment of a 32 channel multiplex TTU system may also include encoders which send 250 position information to an encoder interface. The encoder interface may transmit 252 the scan position information to the interface board. The interface board may combine the received signal data with scan position information to transmit 260 signal and position information over an Ethernet connection to a remote processor. The remote processor may match 262 the received signal to the position information from the encoders to further process and/or analyze the data of the scan.

By multiplexing the channels of a receiver board into one channel, an embodiment of the present invention is capable of including a limited number of subsequent components such as one logarithmic amplifier and one analog-to-digital (A/D) converter. Further, by multiplexing the channels, an embodiment of the present invention is capable of substantial size reduction, such as a unit which may include an interface board, two pulser boards, and two receiver boards for 32 channels in a single box which measures 17" by 18" by 9". For example, a unit may be small enough to mount directly under a scanner, thereby taking up no additional floor space in a factory or at the inspection site.

Embodiments of the present invention are capable of achieving 12 bit analog-to-digital signal conversion, rather than typical 8 bit digital data, thus providing a higher signal-to-noise ratio, i.e., greater sensitivity. Accordingly, a system limited such as by a serial communication connection may only be able to transmit scan data in real time at a resolution of 8 bits, such as where a 0-10V analog signal is converted to a digital signal with values from 0-255 for an analog resolution at 0.039 volts ($10\ V/2^8$). By comparison, a system using improved communications such as a system using an Ethernet connection can transmit scan data in real time at a resolution of 12 bits, such as where a 0-10V analog signal is converted to a digital signal with values from 0-4095 for an analog resolution at 0.00244 volts ($10\ V/2^{12}$). By comparison, the noise of an 8 bit system with 70 dB of dynamic range would be 1 bit or +/−0.276 dB. But the noise of a 12 bit system with 70 dB of dynamic range would only be +/−0.02 dB. A serial communication connection, such as conventional serial links, may not be capable of transferring 12 bits of data in real time. In general, it is preferred to use as high a digital signal resolution as can be resolved from an analog signal, as is typically limited by the noise present in the signal.

Use of Ethernet communication technologies increases the speed of conventional data acquisition by as much as two-fold. Increasing the data acquisition rate may permit faster part scanning which may result in shorter inspection times and decreased inspection costs. For example, current systems with 32 channels may be capable of scanning 5 inches per second. Embodiments of the present invention may be capable of scanning as much as 10 inches per second using 32 channels using conventional Ethernet communication connections.

Embodiments of the present invention are also easily calibrated, due in part to the reduced number of components and the centralized control through a common interface board.

Embodiments of the present invention are easier to troubleshoot than typical multi-channel TTU systems. For example, troubleshooting a multi-channel TTU system with individual components on each channel would require a technician to determine which of the numerous channels is not operational. By comparison, an embodiment of a multi-channel TTU system of the present invention with only five printed circuit boards includes fewer components and fewer circuitry to troubleshoot, essentially reducing the number of variables of possible non-operation. Similarly, because of the reduced components and circuitry, embodiments of the present invention are less expensive to fix than typical multi-channel TTU systems.

An example embodiment of a 32 channel multiplexer of the present invention may use an electronic box measuring 17 inches by 18 inches by 9 inches to retain the electronic components of the 32 channel multiplexer. Because of the high dynamic gains and frequency of the inspection, such as 5 MHz, the RF multiplexer boards, also referred to herein as the receiver boards, may have heavy shielding and provide spacing between components. The interface board which controls the timing requirements for the multiplexing system may include a serial and/or Ethernet connection for communications to a processor, such as a remote computer for controlling pulsing of the transmit transducers and analyzing the received and processed signals. The interface board may also include in signal data packets position and/or distance information from encoders received through an encoder interface, thereby eliminating the need for external encoder boards. Embodiments of the present invention decrease noisy RF cables by providing data digitization at the 32 channel multiplexer and then transmitting the data for analysis through a serial or Ethernet connection. Further, by providing the entire 32 channel multiplexer in such a small housing, the unit may be small enough to be located proximate the scanning system, such as mounted underneath the scanner, thereby avoiding the consumption of additional floor space. These and other features of the present invention make embodiments of the present invention not only convenient, but also efficient and economical multiplexing systems. Particularly, embodiments of the present invention may reduce maintenance costs associated with existing multi-channel TTU equipment, such as by simplifying existing systems to reduce the number of associated components and wiring complexities by incorporating a 32 channel TTU multiplexing system of the present invention. For example, multiplexing technology of the present invention reduces the receive channels into a single channel on each receiver board, thereby requiring only one logarithmic amplifier, one linear amplifier, and one analog-to-digital converter for each receiver board. Further, embodiments of the present invention may be specifically designed for TTU inspection, by comparison to existing systems and/or embodiments which may be designed for pulse echo inspection. For example, electronics and component variables may be selected to provide a high dynamic range, such as 70 dB, to match desired TTU inspection characteristics.

As described more fully herein, provided are systems and methods for multi-channel non-destructive inspection which provides high data throughput, logarithmic amplification of large dynamic range, and simplicity of supporting electronics. More specifically, provided are systems and methods in accordance with embodiments of the present invention for inspecting a structure using an interface board, two pulser boards, each coupled to 16 transmit channels, and two receiver boards, each coupled to 16 receive channels, where the receiver boards are capable of processing data from the 32 receive channels by logarithmically amplifying at least 70 dB of dynamic range. A receiver board may include a serial connection of two layers of multiplexing switches to provide 70 dB isolation between channels, a logarithmic amplifier for logarithmically amplifying 70 dB of dynamic range, a linear amplifier, and an analog-to-digital converter.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for inspecting a structure, comprising:
an interface board;
at least one pulser board communicably coupled to said interface board;
a plurality of transmit channels communicably coupled to said pulser board;
at least one receiver board communicably coupled to said interface board;
a plurality of inspection data receive channels communicably coupled to said receiver board, wherein said receiver board is comprising a logarithmic amplifier for processing inspection data signals from said plurality of inspection data receive channels and providing logarithmic amplification to each channel for at least 70 dB of dynamic range.

2. The system of claim 1, wherein said receiver board further comprises a mulitplexer for providing 70 dB of isolation between inspection data receive channels, and wherein said receiver board is capable of processing data from said plurality of inspection data receive channels with 70 dB of isolation provided by said multiplexer and with logarithmic amplification of 70 dB of dynamic range provided by said logarithmic amplifier.

3. The system of claim 1, wherein said multiplexer is a series of multiplexing chips and wherein said 70 dB of isolation is provided by a 60 dB multiplexing chip serially coupled to a 10 dB multiplexing chip of said multiplexer.

4. The system of claim 3, wherein said multiplexing chips are capable of switching between said inspection data receive channels.

5. The system of claim 3, wherein said logarithmic amplifier is capable of logarithmic amplification of −67 dB to +3 dB of dynamic range.

6. The system of claim 3, wherein said multiplexing chips are capable of switching between said receive channels.

7. The system of claim 3, wherein said logarithmic amplifier is capable of logarithmic amplification of −67 dB to +3 dB of dynamic range.

8. The system of claim 1, wherein said receiver board comprises:
 a plurality of tuned filters, one of said tuned filters communicably coupled to each of said inspection data receive channels;
 a multiplexer serially coupled to said plurality of tuned filters;
 a logarithmic amplifier serially coupled to said multiplexer;
 a linear amplifier serially coupled to said logarithmic amplifier; and
 an analog-to-digital converter serially coupled to said linear amplifier.

9. The system of claim 8, further comprising an envelope peak detector, serially coupled between said linear amplifier and said analog-to-digital converter, for capturing the voltage peaks of the signal that has been multiplexed, logarithmically amplified, and linearly amplified.

10. The system of claim 9, further comprising a diode, serially coupled between said linear amplifier and said envelope peak detector, for isolating positive voltage from the signal that has been multiplexed, logarithmically amplified, and linearly amplified.

11. The system of claim 10, wherein said 10 dB multiplexing chips are capable of switching up to eight inspection data receive channels.

12. The system of claim 8, wherein said multiplexer comprises a series of multiplexing chips, wherein said 70 dB of isolation between inspection data receive channels is provided by a 60 dB multiplexing chip serially coupled to at least one 10 dB multiplexing chip of said multiplexer, and wherein said multiplexer is capable of switching between said plurality of inspection data receive channels.

13. The system of claim 1, wherein said interface board is capable of transmitting digitized data from said receiver board though a communication channel.

14. The system of claim 13, wherein said communication channel comprises an Ethernet communication channel.

15. The system of claim 13, wherein said communication channel is capable of transmitting scan data at a 12-bit resolution.

16. The system of claim 13, wherein said interface board is further capable of transmitting digitized data form said receiver board through said communication channel in real time.

17. The system of claim 1, wherein said interface board is capable of receiving data provided by encoders.

18. The system of claim 17, further comprising an encoder interface communicably coupled to said interface board for receiving data from said encoders and providing said data to said interface board.

19. The system of claim 18, wherein said encoder interface comprises at least one counter chip communicably coupled to said interface board and said encoders.

20. The system of claim 18, wherein said encoder interface is capable of receiving data selected from the group consisting of position data, speed data, velocity data, and distance data.

21. The system of claim 1, wherein said receiver board comprises a logarithmic amplifier serially coupled to a linear amplifier.

22. The system of claim 21, wherein said logarithmic amplifier is capable of −67 dB to +3 dB of logarithmic amplification.

23. The system of claim 21, wherein said linear amplifier is capable of providing 20 dB of linear amplification.

24. The system of claim 1, comprising:
 two pulser boards, each coupled to 16 transmit channels; and
 two receiver boards, each coupled to 16 inspection data receive channels.

25. The system of claim 24, wherein each pulser board is a printed circuit board and comprises 16 pulsers communicably coupled to said 16 transmit channels.

26. The system of claim 1, wherein both said receiver board and said interface board are capable of processing inspection data signals from said plurality of inspection data receive channels at a resolution of 12 bits.

27. The system of claim 1, wherein said interface board and said pulser board are capable of communicating data to said transmit channels at a cycling rate of 200 microseconds (µs) per transmit channel, said receiver board is further capable of receiving and processing data from said inspection data receive channels at a cycling rate of 200 microseconds (µs) per receive channel, and said interface board is further capable of communicating data from said receiver board at a cycling rate of 200 microseconds (µs) per inspection data receive channel.

28. The system of claim 1, wherein said receiver board comprises a tuned filter communicably coupled to each of said inspection data receive channels and capable of processing data at a 5 MHz inspection frequency.

29. A 32 channel multiplexing system for inspecting a structure, comprising:
 thirty-two transmit transducers;
 thirty-two receive transducers capable of receiving signals emitted by said transmit transducers following propagation of said emitted signals through the structure;
 thirty-two receive channels coupled to said receive transducers;
 a multiplexing system coupled to said thirty-two inspection data receive channels and comprising a logarithmic amplifier for processing data from said thirty-two receive transducers transmitted through said thirty-two inspection data receive channels and providing logarithmic amplification to each channel with at least 70 dB of dynamic range.

30. The system of claim 29, wherein said multiplexing system is further adapted to switch between said inspection data receive channels.

31. The system of claim 30, wherein said linear amplification has a 20 dB gain.

32. The system of claim 30, wherein said multiplexing system is further capable of converting from analog to digital said data that has been previously processed with logarithmic amplification and linear amplification.

33. The system of claim 29, wherein said transmit transducers comprise a pulsing sensor and said receive transducers comprise a receiving sensor communicably coupled to a corresponding pulsing sensor, and wherein each pulsing sensor is coupled to a transmit channel and each receiving sensor is coupled to an inspection data receive channel.

34. The system of claim 29, further comprising an interface for remote communication to an analysis computer.

35. The system of claim 29, wherein said multiplexing system is further adapted to filter said data received from said inspection data receive channels before switching and logarithmically amplifying said data.

36. The system of claim 29, wherein said multiplexing system is further capable of linearly amplifying said data that has been previously processed with logarithmic amplification of at least 70 dB of dynamic range.

37. The system of 29, wherein said multiplexing system is further capable of processing data from said thirty-two inspection data receive channels at a cycling rate of 5 kHz to process data from each of said receive channels once every 6.4 milliseconds (ms).

38. The system of claim 29, wherein said multiplexing system is further adapted to convert said data from an analog signal to a digital signal.

39. A method for multiplexing channels of an inspection system comprising repeating the steps of:
   receiving signals from a plurality of inspection data receive channels; and
   multiplexing said received signals, wherein said multiplexing comprises:
      filtering said received signals;
      switching between said plurality of inspection data receive channels to select one inspection data receive channel and define a switched received signal;
      logarithmically amplifying said switched received signal;
      linearly amplifying said switched, logarithmically amplified received signal; and
      converting said switched, logarithmically amplified, linearly amplified received signal from analog to digital;
   correlating the multiplexed signals to a physical structure of a part under inspection; and
   presenting the correlated information on a display for review by a user.

40. The method of claim 37, further comprising the step of transmitting signals to a plurality of transmit channels.

41. The method of claim 40, further comprising the steps of:
   controlling timing requirements for said step of transmitting signals to a plurality of transmit channels; and
   transmitting said multiplexed signals in real time to a remote processor.

42. The method of claim 41, wherein said step of transmitting said mulitpelxed signals in real time to a remote processor comprises the step of transmitting said multiplexed signals from said inspection data receive channels at a cycling rate of 200 microseconds (µs) per inspection data receive channel, and wherein said multiplexed signals are represented by 12 bit signals.

43. The method of claim 40, wherein the step of transmitting signals to a plurality of transmit channels comprises the step of communicating data to said transmit channels at a cycling rate of 200 microseconds (µs) per transmit channel.

44. The method of claim 39, further comprising the step of capturing peak voltage of said switched, logarithmically amplified, and linearly amplified received signal.

45. The method of claim 44, further comprising the step of isolating positive voltage from said switched, logarithmically amplified, and linearly amplified received signal prior to the step of capturing peak voltage.

46. The method of claim 39, wherein the step of logarithmically amplifying said switched received signal comprises providing logarithmic amplification for at least a 70 dB of dynamic range.

47. The method of claim 46, wherein the step of providing logarithmic amplification for at least 70 dB of dynamic range comprises providing amplification from −67 dB to +3 dB.

48. The method of claim 39, further comprising the step of processing said multiplexed signals from said inspection data receive channels at a cycling rate of 200 microseconds (µs) per inspection data receive channel.

49. A system for inspecting a structure, comprising:
   an interface board;
   at least one pulser board communicably coupled to said interface board;
   a plurality of transmit channels communicably coupled to said pulser board;
   at least one receiver board communicably coupled to said interface board; and
   a plurality of receive channels communicably coupled to said receiver board, wherein said receiver board is comprising a logarithmic amplifier for processing signals from said plurality of receive channels and providing logarithmic amplification to each channel for at least 70 dB of dynamic range,
   wherein said receiver board further comprises a mulitplexer for providing 70 dB of isolation between inspection data receive channels, and wherein said receiver board is capable of processing data from said plurality of inspection data receive channels with 70 dB of isolation provided by said multiplexer and with logarithmic amplification of 70 dB of dynamic range provided by said logarithmic amplifier, and
   wherein said multiplexer is a series of multiplexing chips and wherein said 70 dB of isolation is provided by a 60 dB multiplexing chip serially coupled to a 10 dB multiplexing chip of said multiplexer.

* * * * *